United States Patent [19]

Schlensog et al.

[11] Patent Number: 4,573,969

[45] Date of Patent: Mar. 4, 1986

[54] BREAST PUMP

[75] Inventors: Klaus Schlensog, Cham; Christian Beer, Boniswil; Robert Riedweg, Lucerne, all of Switzerland

[73] Assignee: Ameda AG, Zug, Switzerland

[21] Appl. No.: 567,891

[22] Filed: Jan. 3, 1984

[30] Foreign Application Priority Data

Jan. 11, 1983 [CH] Switzerland .......................... 122/83

[51] Int. Cl.⁴ .............................................. A61M 1/06
[52] U.S. Cl. ...................................... 604/74; 604/231
[58] Field of Search ................................. 604/74–76, 604/231

[56] References Cited

U.S. PATENT DOCUMENTS

| | | | |
|---|---|---|---|
| 897,289 | 9/1908 | Howell | 604/74 |
| 3,822,703 | 7/1974 | Davisson | 604/75 |
| 3,977,405 | 8/1976 | Yanase | 604/74 |
| 4,311,141 | 1/1982 | Diamond | 604/74 |

FOREIGN PATENT DOCUMENTS 836560  4/1952  Fed. Rep. of Germany ........ 604/74

*Primary Examiner*—Dalton L. Truluck
*Attorney, Agent, or Firm*—Werner W. Kleeman

[57] ABSTRACT

A breast pump for manual operation of the type comprising a receptacle that is put against the breast to surround a teat and has a variable enclosed volume in the manner of a cylinder-and-piston-pump which when operated in contact with a breast causes the milk to be drawn into the receptacle due to the suction generated by an enlargement of the enclosed volume.

The tubular part of the hollow piston is tapered such that its upper end has a smaller outer diameter than its lower end that carries an annular lip seal; consequently, the outer cylinder which is manipulated, i.e. moved to-and-fro relative to the hollow piston, can be tilted to some extent without concurrent tilting of the piston and the suction bell that is integrally connected therewith; thus, pump-induced motion of or at the sensitive area of teat and areola is minimized for improved user comfort. The suction bell is arranged at a predetermined angle with respect to the longitudinal axis of the tapered tubular part so that the outer cylinder can be held more nearly vertical when the pump is used in a normal sitting position; back-flow of the milk from the reservoir to the breast can be reduced or eliminated.

9 Claims, 9 Drawing Figures

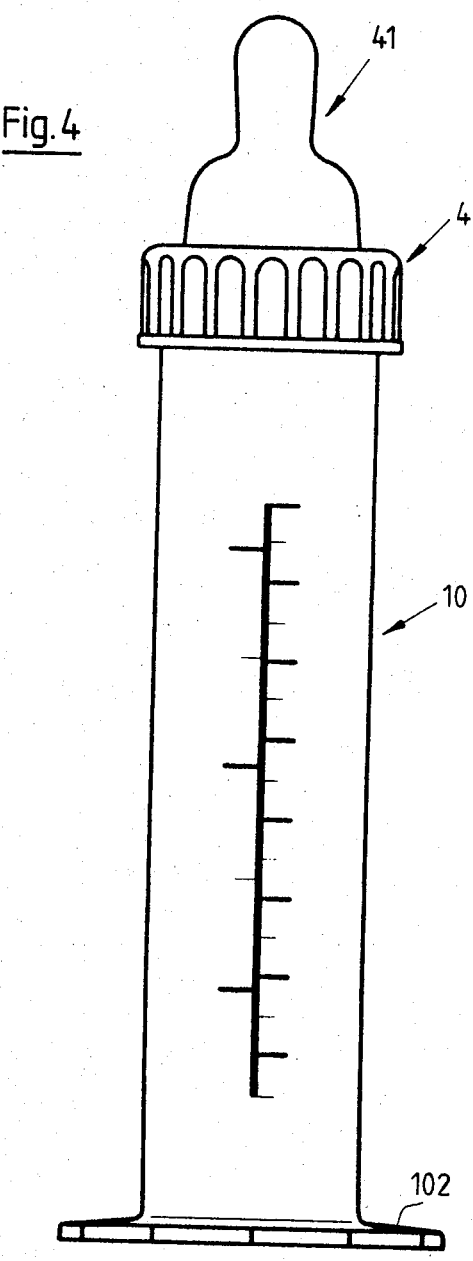
Fig. 4
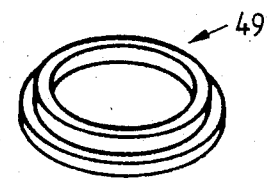
Fig. 4a
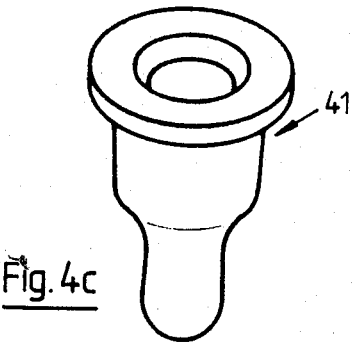
Fig. 4b
Fig. 4c

BREAST PUMP

BACKGROUND OF THE INVENTION

The present invention generally relates to breast pumps and specifically to an improvement in manually operated breast pumps.

Increasing numbers of women are choosing to feed their babies with mother's milk and it is widely assumed that both the preference of the natural product over substitutes as well as the bodily contact during breast-feeding are best for the infant. Frequently, however, there is an at least temporary need for a breast pump; for example, a mother who delivers her infant prematurely will pump her breast so that the colostrum and milk can be fed to the premature infant having a particular need for the protective factors known to be contained in colostrum and normal mother's milk.

Other circumstances that indicate the use of a breast pump include temporary hospitalization of either mother or child, a flat or inverted shape of the nipple as well as other physiological factors and, last but not least, the problems of supplying an infant with mother's milk when the mother continues or commences to work outside the house.

Two main types of conventional breast pumps are to be distinguished depending upon how the pressure reduction (also called "negative pressure" or "suction pressure") within the suction bell that is put onto the breast will be generated, i.e. either by means of an electrical motor or manually.

The term "suction bell" is used herein to refer to any open-ended structure having an opening at the end of a hollow and generally convergent structure with a linear or curved taper providing sufficient space to fit onto a breast around the nipple or teat without having direct contact with neither teat nor areola; of course, a suction bell is a structural feature common to motorized as well as manually operated breast pumps.

Another common feature of most breast pumps is some kind of reservoir or space for holding the pumped-off milk. Thus, a conventional pump comprises the suction bell connected with a reservoir, such as a bottle, and with a source of negative pressure for causing a sufficient but not overly strong and preferably easily controllable suction; typically, such suction is defined by the ambient atmospheric pressure minus the "negative pressure" or "suction pressure" of, say, 0.01 to 0.3 bar.

In all conventional breast pumps for manual operation suction is produced by means of a hollow space or cavity having a variable enclosed volume; a typical example of such a suction means is a rubber ball or bulb that can be manually compressed and tends to recover its original shape when not compressed by hand. Such a ball or bulb, optionally provided with a one-way valve, can be connected directly with a suction bell to serve as a simple breast pump if the internal volume of the suction bell is sufficient so that it can act as a temporary milk reservoir.

A main disadvantage of manually operated breast pumps having such rubber-ball-type suction means is that sterility cannot be maintained and certainly not visually controlled. In that respect breast pumps of the "coaxial" type disclosed in U.S. Pat. No. 3,977,405 issued Aug. 31, 1976, to Shozaburo Yanase provide the advantage of being made of a sterilizable transparent polymer, e.g. a polycarbonate, or of ordinary glass so that sufficient sterility can be easily obtained, e.g. by boiling in water, and visually controlled.

Briefly, a prior art coaxial breast pump of the type disclosed in the U.S. Patent to Yanase just mentioned works in the manner of an inversely operated syringe such as disclosed in U.S. Pat. No. 3,886,928, issued June 3, 1975 to Sarstedt except that the piston element is hollow and carries the suction bell. Hence, the mother's breast serves to close the hollow piston element of a breast pump of the coaxial type.

Generally, the coaxial-type breast pump disclosed in the U.S. Patent to Yanase comprises an inner and an outer cylinder and a packing on the outside of the inner cylinder to seal up a clearance between the inner and outer cylinders; the inner cylinder has two open ends, one end being divergent so as to form a suction bell which is put against a breast while the other end is inserted into the outer cylinder and displaced therein. The outer diameter of the inner cylinder is smaller than the inner diameter of the outer cylinder to permit the displacement of the inner cylinder in the outer cylinder and the outer cylinder is a container with an open end and a closed end.

Prior art breast pumps of this coaxial type have been found to suffer from two disadvantages: when the pump is used in an erect sitting position, i.e. with the thorax in an upright or substantially vertical position, the longitudinal axis of the outer cylinder will be nearly horizontal or slightly inclined, say at an angle of 10° to 20°. In such a position of the outer cylinder—which serves as the milk reservoir—even a minor amount of milk will fill the reservoir to the extent that back-flow of the milk from the inclined reservoir towards the breast will occur.

Such back-flow is quite undesirable because bacterial, viral or other contaminants on the skin will be washed into the milk. Further, as back-flow of milk may cause an uncomfortable sensation, the mother using such a pump will either tend to incline her thorax in a forward direction so as to increase the angle between the teat axis and the horizontal, or she will attempt to tilt the outer cylinder relative to the teat axis; as teat and areola of the breast of a nursing mother are extremely sensitive, such tilting of the milk reservoir of a coaxial pump is neither generally feasible nor normally free of discomfort. Almost needless to say that a coaxial pump of the type disclosed in U.S. Pat. No. 3,977,405 cannot be used at all when the thorax of the person using the pump is inclined backwards such as when at rest on a bed or in a backwards inclined chair.

The other main disadvantage of prior art coaxial breast pumps as disclosed in U.S. Pat. No. 3,977,405 is a substantially rigid motional coupling of the inner and the outer cylinder when the latter is tilted. In other words, any voluntary or involuntary motion of the user's hand that will cause "tilting" of the longitudinal axis of the outer cylinder (i.e. any angular change of the position of that axis relative to a line of reference, e.g. the breast or teat axis) will cause about the same tilting of the inner cylinder and, thus, of the longitudinal axis of the suction bell. This, in turn, will, at best, cause an irregularity in the distribution of the pressure of contact between suction bell and breast or, at worst, a tilting stress on the teat and/or the areola which in many instances will cause pain in these most sensitive breast areas.

SUMMARY OF THE INVENTION

Hence, it is a primary object of the present invention to provide a new and improved breast pump for manual operation of the cylinder-and-piston or generally coaxial type which is not afflicted with the aforementioned drawbacks and limitations of comparable prior art breast pumps.

Another important object of the present invention is to provide an improvement in the construction of manually operated breast pumps so that tilting of the hand-held outer cylinder of the pump will not cause commensurate tilting of the longitudinal axis of the suction bell.

A further important object of the present invention aims at improving manually operable breast pumps of the generally coaxial type so as to reduce or eliminate back-flow of milk from the reservoir to the breast when the thorax of the user is in an upright or even in a backwards inclined position.

Now, in order to implement these and still other objects, which will become more readily apparent as the description proceeds, the present invention provides a breast pump of the type suitable for extraction of mother's milk by means of a receptacle having a variable enclosed volume when in contact with a breast and being capable of generating a suction effect upon manual variation of enclosed volume. The pump operates in the manner of a cylinder-and-piston system of the generally coaxial type comprising an elongated cylinder having a first or lower closed end and a second or upper open end as the outer pump means. Further, the pump has a hollow piston including a suction bell portion suitable for putting against a mother's breast to surround a nipple thereof and an elongated tubular portion integrally connected with the suction bell; the lower end of the tubular portion is open and carries a resilient sealing ring on its outer surface. The elongated tubular portion is inserted into the outer cylinder for reciprocating displacement relative to the cylinder in a substantially axial direction of the latter so that there is a relative to-and-fro motion between the open end of the tubular portion and the closed end of the cylinder while the resilient sealing engages with the inner surface of the outer cylinder to generate a suction effect upon any fro movement.

In normal use of the pump the suction bell and, hence, the lower open end of the tubular portion will be substantially at rest while the lower closed end of the outer cylinder will be manipulated to move to-and-fro.

Now, in order to uncouple the substantially rigid connection as regards tilting between an outer cylinder and a tubular member slidingly arranged therein, the tubular portion of the piston means of an inventive breast pump is tapered in a preferably continuous and essentially linear manner such that its outer diameter at its open lower end is greater than its outer diameter at the junction with the suction bell; a considerable degree of tilting of the longitudinal axis of the outer cylinder will be possible relative to the longitudinal axis of the elongated tubular portion, or—in other words—the outer cylinder can be tilted to some extent, say up to 20°, without substantially tilting of the suction bell even though this bell is an integral part of the hollow piston, i.e. rigidly connected therewith.

It will be understood that such uncoupling of tilting motion unintentionally caused by manipulation of the outer cylinder considerably increases the user comfort because there will be substantially less tilting, if any, of the longitudinal axis of the suction bell and, hence, less motional stress of the teat and areola region. Furthermore, such uncoupling of tilting motion is advantageous for the angular arrangement of the suction bell (i.e. with reference to its longitudinal axis) as provided by another important feature of the inventive breast pump; briefly, in order to eliminate or reduce the flow-back tendency of milk contained within the outer cylinder towards the breast, the suction bell portion of the hollow piston in a breast pump according to the invention is arranged at a predetermined angle relative to the longitudinal axis of the tubular portion. In contrast with conventional coaxial breast pumps where the suction bell portion is formed by a cone that is coaxial with the inner tube, the suction bell portion of the inventive breast pump is "cranked" or "angularly offset" by an angle of typically between 30° and 90°, preferably about 70°. This angle termed "$\alpha$" is the smaller angle portion enclosed between the longitudinal axis of the suction bell and the longitudinal axis of the elongated tubular portion of the hollow piston as will be explained in more detail below.

The suction bell portion generally has rotational symmetry about its longitudinal axis. Preferably, such bell portion is formed by two adjacent cones of different cone angles, e.g. a first cone face having a cone angle (enclosed between opposite cone faces) of from about 110° to 150° and preferably about 130° in the bell area for contact with the breast, and a second cone face of from about 30° to 60° and preferably about 45° in the bell area surrounding the teat. Preferably, a protrusion or shoulder is provided at the inside of the hollow piston, generally near the area thereof where the integrally connected suction bell portion joins the elongated tubular portion of the hollow piston; such a shoulder is useful as an additional safeguard against back-flow of milk, i.e. when the outer cylinder is held at an inclination of substantially less than 90° relative to the horizontal, e.g. at an angle of between 80° and 30° relative to the horizontal as may be the case when the thorax of the user is inclined backwards.

A most preferred embodiment of the protruding shoulder is a continuation of a portion of the second cone face explained above beyond its line of intersection with the elongated tubular portion of the hollow piston. Such continuation may protrude to the extent that up to about 80% and preferably about 50% of the inner cross-sectional area of the tubular portion are covered by the protrusion which then will act as back-flow bar that is effective even if the pump is used by a person lying on a bed or sitting in a comfortably reclined position.

According to another preferred embodiment of the inventive breast pump the outer cylinder thereof is provided at its open end with a screw cap; the top face of the cap is provided with a central opening of a diameter or width that is somewhat greater than the largest outer diameter of the elongated tubular portion but somewhat smaller than the outer diameter of the annular sealing. As will be easily understood, such a cap has the advantage of serving as a stop against unintended withdrawal of the hollow piston from the cylinder. Of course, the piston can be removed by unscrewing the cap, and the piston-cap-assembly can be disassembled easily either by forcing the resilient annular seal through the cap or by first removing the sealing ring from the piston and then withdrawing the tubular piston portion from the cap.

Preferably, the annular sealing means is a conventional lip sealing ring, e.g. as disclosed in the above mentioned U.S. Pat. No. 3,977,405, and is removably arranged in a groove at the outer surface of the tubular piston portion near the open lower end thereof.

Generally, both the outer cylinder as well as the hollow piston of the breast pump will be made of a substantially rigid and transparent polymer capable of withstanding boiling water at ambient pressure for simple cleaning and sterilization. The term "substantially rigid" as used herein is intended to exclude pliability or easy flexibility of a material when used at a thickness of at least about 1 mm. This does not exclude the use of materials that may be pliable or easily flexible when in the form of a film. Organic polycarbonates of various types and proveniences are an illustrative example of a suitable material for use in manufacturing the outer cylinder and the hollow piston of a breast pump according to the invention.

For improved fit or adaption of the suction bell to smaller breasts a removable yet substantially rigid insert or adapter lining having a similar geometrical shape as the suction bell but of somewhat smaller dimensions can be provided and preferably is made of the same material as the hollow piston. No particular fastening means are required for such adapters if the smaller cone angle of the outer surface of the insert substantially matches or interfits with the smaller cone angle of the suction bell.

BRIEF DESCRIPTION OF THE DRAWINGS

The invention will be better understood and objects other than those set forth above will become apparent when consideration is given to the following detailed description thereof. Such description makes reference to the annexed drawings which illustrate preferred exemplary embodiments of the invention and wherein:

FIGS. 4, 4a, 4b and 4c illustrate the use of the outer cylinder of the pump of FIG. 1 as the container portion of a conventional feeding bottle arrangement further comprising a securing ring (4a), a covering lid (4b) and a rubber nipple (4c).

DETAILED DESCRIPTION OF THE PREFERRED EMBODIMENTS

Figure 1:
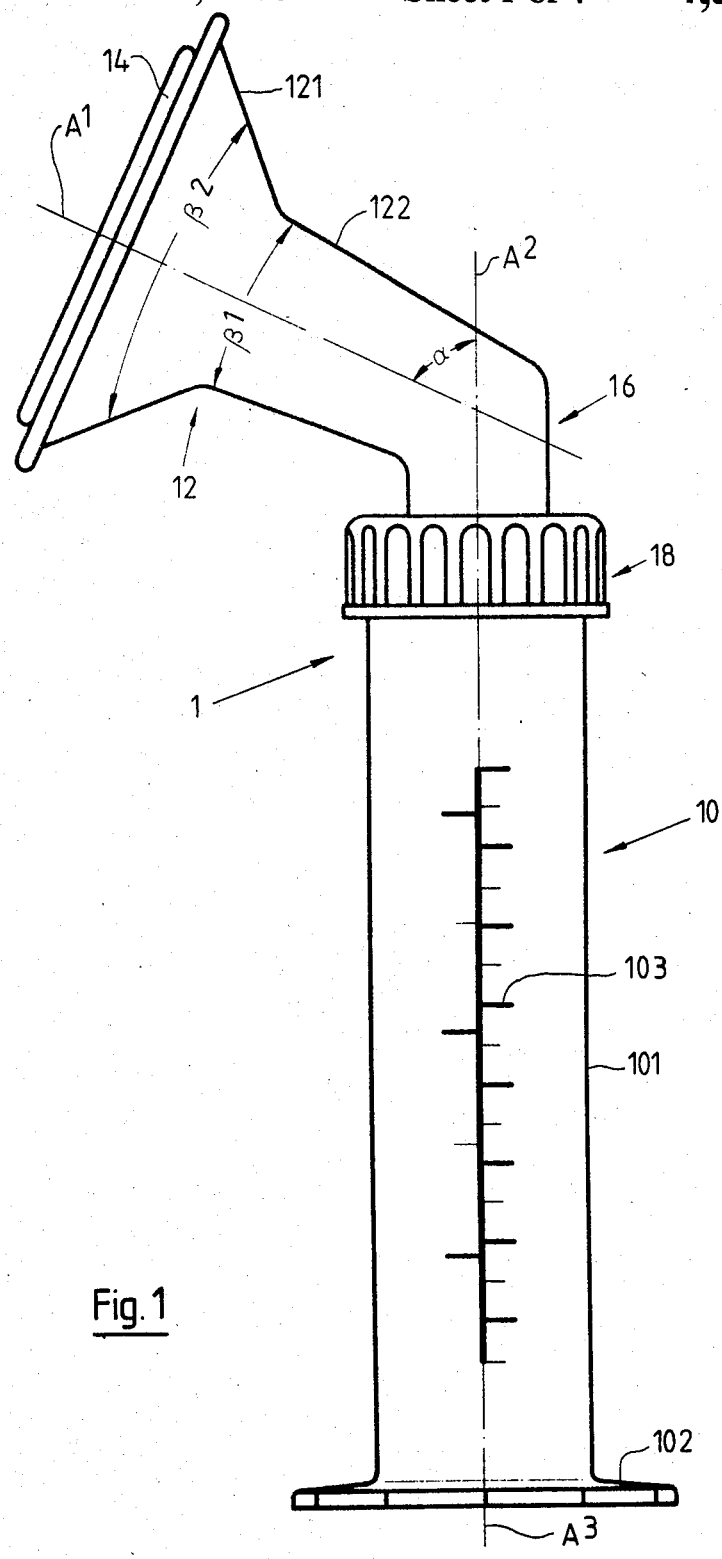
FIG. 1 is a side view of a breast pump according to the invention provided with a screw cap as a stop means to prevent unintended separation of cylinder and piston.

Describing now the drawings, the breast pump 1 illustrated by way of example in FIG. 1 in a side view and in about normal natural size comprises the outer cylinder 10 consisting of a cylindrical tube 101 having a closed lower end 102 and being made of a transparent heat-sterilizable material such as mineral (inorganic) glass or a heat-resistant transparent organic polymer (organic glass), such as an organic polycarbonate.

Figure 3:
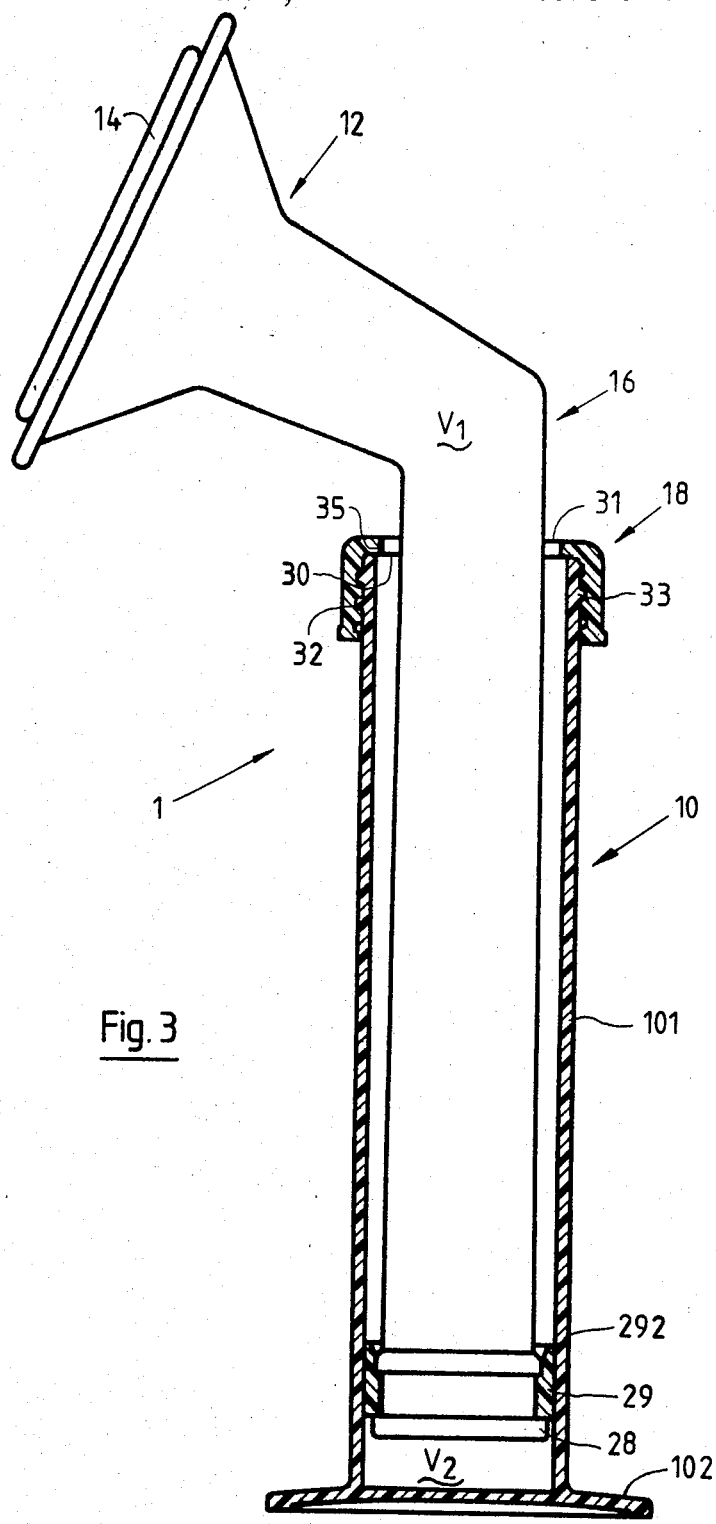
FIG. 3 is a side view of the breast pump shown in FIG. 1 with the outer cylinder shown in section.

Preferably, cylinder 10 is a monolithic structure comprising the upright tube 101 having a homogeneous wall thickness of typically in the range of from about 1 to about 3 mm and the bottom closure in the form of base plate 102 of circular or polygonal shape; as shown in FIG. 3, the tube portion that forms the upper end 30 of cylinder 10 is provided at its outer surface with a thread 33 for engagement with a holding ring or screw-cap 18 that has a matching inner thread 32 and a circular opening or aperture 31 at its upper face. As is also apparent from FIG. 3, there is a gap of substantial width between the outer wall of elongated inner tubular part 16 and the inner wall of cylinder 101 or the inner edge of opening 31 in cap 18. The width of this gap decreases as the outer diameter of tubular portion 16 increases in the direction from bell 12 towards seal 29 and axial tilting of tubular portion 16 within cylinder 10 is possible in any position of axial displacement of portion 16 within cylinder 10. The definition and consequence of such tilting will be explained in more detail below.

However, it will be apparent already that ring 18 will act as a stop means against complete unintentional withdrawal of inner tube 16 from cylinder 10 because seal 29 will not, or not easily, pass through aperture 31. While such stop means is a generally preferred feature of the inventive breast pump, it is not absolutely essential; when a ring 18 is used it should consist of a heat sterilizable and preferably somewhat elastic organic polymer such as polypropylene, polyamide, polyacetal or a similar synthetic material or plastic.

Figure 2:
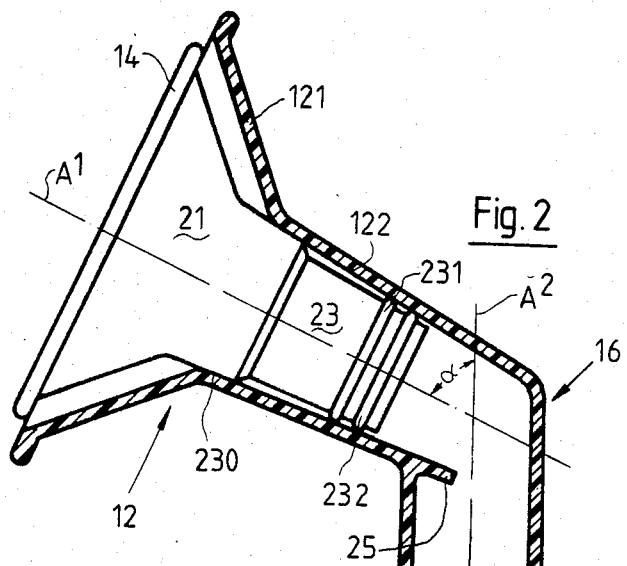
FIG. 2 is a partially sectioned side view of the piston, of the pump of FIG. 1 plus annular seal.
Figure 2:
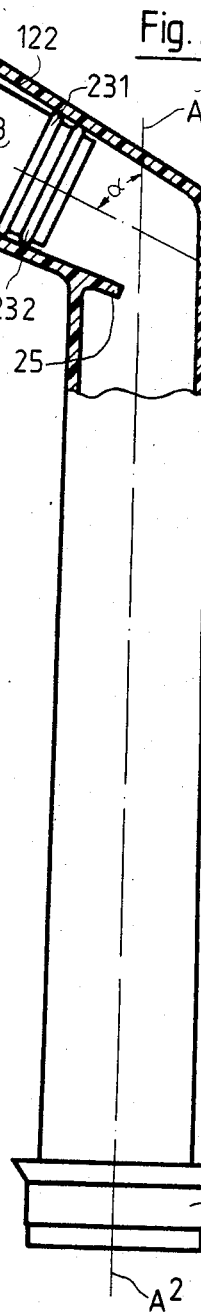

The hollow piston that is inserted into cylinder 10 of the breast pump shown in FIG. 1 as separately shown in FIG. 2 carries a substantially conical suction bell 12 integrally connected with tubular portion 16 in a "cranked" or angularly offset arrangement; the spatial or angular position of suction bell 12 relative to tube 16 can be best defined by the longitudinal axis $A^1$ of bell 12 and the longitudinal axis $A^2$ of tube 16. As apparent from FIG. 1, the suction bell axis $A^1$ is offset by the angle $\alpha$ relative to tube axis $A^2$. This angle $\alpha$ will be in the range of from about 30° to about 90°, preferably about 60° to 70°, 65° being particularly preferred.

It will be understood that in normal use of any breast pump the longitudinal axis of the suction bell will be in a substantially coaxial alignment with the teat axis which in the case of a lactating breast will have an inclination in the range of from about 0° to about 30° from the horizontal when the thorax is in a substantially upright or vertical position.

However, in a conventional and fully coaxial breast pump where the longitudinal axis of the suction bell is in a substantially coaxial alignment with the longitudinal axis of the hollow piston and—because of substantially rigid motional coupling explained above—also with the longitudinal axis of the outer cylinder, such a pump must be held nearly horizontal or at an angle of up to 30° down from the horizontal when the thorax of the user is upright. Hence, the user will tend to lean forward as soon as some milk has collected in the outer cylinder because she will normally try to avoid that the milk in the container flows back to and contacts the breast.

A pump according to the invention as shown in FIG. 1 can be held nearly vertical by a user whose thorax is in a upright position without problems of back-flow.

While back-flow of milk in an inventive pump can be effectively prevented even when the user leans backwards as will be explained below, it should be noted that the angular offset of the suction bell in a breast pump according to the invention must be combined with some tiltability, at least, of the outer cylinder relative to the hollow piston if full user comfort is to be achieved because angular offset of the suction bell relative to the direction of the displacement of piston and cylinder needed to cause a pumping effect may somewhat diminish control of optimum alignment of suction bell axis and teat axis. For that reason, the entire piston element of the inventive pump, i.e. its tube axis $A^2$, is tiltable relative to the longitudinal axis $A^3$ through the center of tube 101 of cylinder 10 because of the predetermined gap between tube 16 and cylinder 10; due to the fact that the outer diameter of tube 16 is smaller at its upper end (adjacent suction bell 12) than at its lower end (adjacent seal 29) such tiltability is maintained in all positions of tube 16 within cylinder 10, and a generally uniform taper of tube 16 so that its outer diameter decreases continually from its seal-carrying lower end to its bell-carrying upper end is the preferred manner of maintaining a generally homogeneous tiltability regardless of the axial displacement.

In practice, the length:width ratio of cylinder 10 should be above 2:1, e.g. in the range of from 4:1 to 6:1. Further, as cylinder 10 must be manipulated for pumping by the user, the outer diameter of the tubular cylinder wall 101 must fit well into a woman's hand; hence, the outer diameter of tube 101 is limited to a maximum of about 60 mm; a typical outer diameter of tube 101 is in the range of from 30 to 40 mm.

The actual amount of milk within cylinder 10 can be visually determined by means of a scale 103 to indicate amounts typically between about 20 ml and about 90 ml; in an essentially vertical position of cylinder 10 a milk portion near full capacity will not lead to back-flow of the milk into contact with the breast.

In order to prevent such back-flow when the cylinder 10 is not held in an essentially vertical position, the invention according to a most preferred embodiment provides for an additional back-flow stop as illustrated by an internally protruding hollow shoulder 25 at the junction of suction bell 12 and tubular portion 16 of the hollow piston of pump 1. As can be seen from FIGS. 1 and 2, suction bell 12 comprises a first cone portion 121 intended for physical contact with a breast; as a consequence, the cone angle of cone portion 121 is relatively wide and typically in the range of from about 110° to about 150° and preferably is about 130°; the second cone portion 122 of bell 12 is intended to surround the teat of a breast in a preferably concentric manner. There may be some local physical contact between a side portion of the teat and the inner surface of cone portion 122 but this is not the rule. On the other hand, a certain longitudinal extension of cone portion 122 is desirable to safely preclude that the front part of the teat abuts at a wall portion of bell 12. Generally, the second cone portion will have a cone angle in the range of from about 30° to about 60° and preferably is about 45°. It will be understood that the term "cone angle" is defined by the angle enclosed between opposite portions on the inner surface of cones 121 and 122.

Shoulder 25 can be formed simply by a continuation of the lower half or shell 230 of the second cone portion 122 beyond the line of junction with tubular portion 16. In FIG. 2 shoulder 25 is shown to cover about a third (~30%) of the inner diameter of tube 16 but it is apparent that the shoulder may protrude towards axis $A^2$ or beyond that axis to cover 50% or even 80% of the inner diameter of tube 16.

Now, assuming that a hollow piston as shown in FIG. 2 having a protruding inner shoulder 25 is inserted in an outer cylinder inclined toward the vertical by about 45°: when $A^2$ and $A^3$ are coaxial, the bell axis $A^1$ will be inclined below the horizontal and such position of the suction bell would not have been operative at all with a conventional coaxial breast pump even though such position would be coincident with the position of the teat axis of a mother's breast when sitting in a comfortably reclined position. In contrast to prior art coaxial structures, the inventive pump 1 with an internal shoulder 25 can be used safely, i.e. without back-flow of milk to the breast, in such reclined position even if the pump contains a substantial or near-capacity portion of milk within cylinder 10.

According to another preferred feature the suction bell 12 of a breast pump 1 according to the invention is provided with a removable adapter or lining 14 of a generally similar geometric shape as the bell 12.

Thus, adapter 14 is comprised of a first cone portion 21 with a relatively wide cone angle as indicated above for contact with the breast, and a second cone portion 23 with a more narrow cone angle for surrounding a teat. Annular ribs or protrusions 231, 232 may be provided at the outer surface of the second cone portion 23 of adapter 14 to sealingly coact with the inner surface of bell 12 for retaining adapter 14 therein and preventing a by-pass of the suction pressure.

As will be understood, such an adapter can be provided as an accessory part for a standard breast pump 1 having a bell 12 dimensioned as explained above and fitting any normal or even an extremely large breast while the adapter 14 would fit with extremely small or/and flat breasts.

Figure 2A:
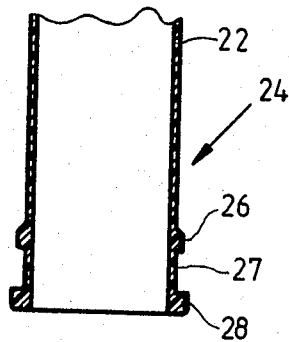
FIGS. 2a and 2b are sectional views of the lower piston, end and of the sealing means shown in FIG. 2.
Figure 2B:
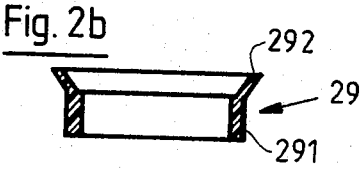

The lower end part 24 of tubular portion 16 plus sealing means 29 is shown in more detail in FIGS. 2a, 2b illustrating an annular groove 27 formed at the outer surface of tube 22, e.g. between two protruding ribs 26, 28.

Groove 27 is dimensioned to receive and retain the annular body portion 291 of sealing ring 29 which is provided with a lip 292 to coact with the inner surface of cylinder 10 in the manner of a one-way valve. Sealing ring 29 consists, for example, of a natural or synthetic elastomer that is resistant against normal sterilizing conditions such as boiling water or steam of up to about 120° C., such as vulcanized synthetic or natural rubber.

Lip portion 292 of seal 29 should be flexible to the extent that the lower end 24 of tube 16 can be moved toward the closed lower end of cylinder 10 without causing any significant compression within the internal space ($V_1+V_2$, cf. FIG. 3) of pump 1 when bell 12 is closed by a breast. On the other hand, upon withdrawal of end 28 in axial direction from cylinder 10, lip 292 will sealingly contact the inner surface of wall 101 of cylinder 10 so that any increase of the internal space ($V_1+V_2$) of pump 1 applied in sealing contact to a breast causes a suction pressure as defined above.

Generally, the variable internal space of pump 1 is defined by the essentially constant inner volume $V_1$ of the hollow piston and the variable inner volume $V_2$ between the closed end of cylinder 10 and the end of tube 16. To-and-fro motion of the closed end of cylinder 10 thus will cause a concurrent change of volume $V_2$ and, thus, of the total inner volume $V_1+V_2$ of pump 1, but due to lip seal 29 only an increase of that volume will cause a significant pressure change within the pump.

It will be understood that a one-way-action of seal 29 is preferred but not absolutely essential.

For the typical use of a breast pump according to the invention the mother will put the suction bell with one hand onto her breast and hold the bell in a comfortable position, i.e. evenly surrounding the areola; with her other hand she will gently pull cylinder 10 from the position shown in FIG. 3 so as to increase volume $V_2$ while keeping the degree of suction just sufficient to cause milk to flow through the teat into cylinder 10.

Downward motion of cylinder 10 and, hence, further increase of $V_2$ will be limited by contact of lip 292 with the shoulder 35 of ring 18 thus precluding an unintended disassembly of the pump.

When cylinder 10 is filled to the extent desired, ring 18 will be unscrewed and put away together with the hollow piston. Then, cylinder 10 can be closed with a second holding ring 48 (cf. FIG. 4a) supplied together with a closure lid or plate 49 (FIG. 4b) and a rubber nipple 41 (FIG. 4c); closure plate 49 will be used only when the milk is to be stored and sealingly enclosed prior to feeding, and replaced for feeding of the infant by nipple 41 to constitute, with cylinder 10, an ordinary feeding bottle as depicted in FIG. 4.

Of course, any accessory of the type shown in FIGS. 4a, 4b, 4c should be made of a sterilizable, i.e. sufficiently heat-resistant material so that any part that may come into contact with the milk can be sterilized. In this context it should be mentioned that the sealing ring 29 should be sufficiently flexible for removal from the lower end 24 of tubular portion 16 prior to cleaning and sterilization.

While there are shown and described present preferred embodiments of the present invention, it is to be distinctly understood that the invention is not limited thereto but may be embodied and practiced within the scope of the following claims. ACCORDINGLY,

What we claim is:

1. In a breast pump comprising:
    an elongated outer cylinder means having a first or lower closed end and a second or upper open end;
    a hollow piston means having
        a suction bell portion for putting against a mother's breast to surround a teat,
        an elongated tubular portion integrally connected at its first or upper end with said suction bell portion and having a second or lower open end, and
        a resilient annular sealing means mounted at the outer side of the tubular portion near said lower end thereof;
    said elongated tubular portion being inserted into said outer cylinder means for reciprocating displacement relative to said cylinder means in a substantially axial direction so as to move said closed lower end of said cylinder means to-and-fro relative to said open lower end of said tubular portion; and
    said sealing means cooperating with said outer cylinder means to generate a suction effect upon said fro movement;
the improvement consisting substantially of: said elongated tubular portion being tapered substantially over the entire length thereof so that its outer diameter at its upper end is smaller than its outer diameter at its lower end for permitting limited tilting of the longitudinal axis of said outer cylinder means relative to the longitudinal axis of said elongated tubular portion, and said suction bell portion being arranged at predetermined angle α of from about 30° to about 90° with respect to the position of the longitudinal axis of said suction bell portion in relation to the longitudinal axis of said tubular portion for permitting the outer cylinder to be held more nearly vertical when said pump is operated to extract milk from the breast of a person whose thorax is in a substantially vertical or upright position.

2. The breast pump of claim 1 wherein said angle α of said longitudinal axis of the suction bell portion relative to said longitudinal axis of said tubular portion is in the range of from about 60° to about 70°.

3. The breast pump of claim 1 wherein said suction bell portion comprises a first cone portion having a cone angle in the range of from about 110° to about 150° in the bell area for contact with said breast and a second cone portion having a cone angle in the range of from about 30° to about 60° in the bell area for surrounding said teat.

4. The breast pump of claim 1 wherein a protruding shoulder is provided at the inside of said hollow piston means near a junction between said suction bell portion and said elongated tubular portion for preventing backflow of milk to the breast when said outer cylinder is tilted from a substantially vertical position.

5. The breast pump of claim 1 wherein a screw cap is provided at the upper end of said outer cylinder means, said screw cap having at its top face a circular opening with an inner diameter that is larger than the outer diameter of the elongated tubular portion near its lower end but is smaller than the outer diameter of the resilient sealing means so as to act as a stop means for said to-and-fro movement.

6. The breast pump of claim 1 wherein said resilient sealing means is a lip seal ring removably mounted in a groove at the outer surface of said elongated tubular portion near said lower end thereof.

7. The breast pump of claim 3 wherein said suction bell portion comprises a removable and substantially rigid adapter lining for an improved fit when used on a smaller breast.

8. The breast pump of claim 1 wherein said longitudinal axis of said outer cylinder means is capable of being tilted by an angle of up to about 20° substantially without concurrent tilting of the longitudinal axis of said suction bell.

9. In a breast comprising:
    an elongated outer cylinder means having a lower closed end and an upper open end;
    a hollow piston means having
        a suction bell portion for placement against a mother's breast to surround a teat,
        an elongated tubular portion integrally connected at upper end with said suction bell portion and having a lower open end, and
        a resilient annular sealing means mounted at the outer side of the elongated tubular portion near said lower open end thereof;
    said elongated tubular portion being inserted into said outer cylinder means for reciprocating displacement relative to said outer cylinder means in a substantially axial direction so as to move said lower closed end of said outer cylinder means to-and-fro relative to said lower open end of said tubular portion; and
    said sealing means cooperating with said outer cylinder means to generate a suction effect upon said fro movement;
    the improvement comprising: said elongated tubular portion being tapered substantially over the entire length thereof so that its outer diameter at its upper end is smaller than its outer diameter at its lower end for permitting limited tilting of the longitudinal axis of said outer cylinder means relative to the longitudinal axis of said elongated tubular portion;

said suction bell portion being arranged at a predetermined angle α in the range of about 30° to about 90° with respect to the position of the longitudinal axis of said suction bell portion in relation to the longitudinal axis of said elongated tubular portion for permitting the outer cylinder means to be held more nearly vertical when said pump is operated to extract milk from the breast of a person whose thorax is in a substantially upright position; and a protruding shoulder provided at the inside of said hollow piston means near a junction between said suction bell portion and said elongated tubular portion for preventing back-flow of milk to the breast when said outer cylinder means is tilted from a substantially vertical position.

* * * * *